United States Patent
Kantor et al.

(10) Patent No.: US 10,245,437 B2
(45) Date of Patent: Apr. 2, 2019

(54) SYSTEM AND METHOD FOR PROVIDING NONINVASIVE VENTILATION

(71) Applicant: INOVYTEC MEDICAL SOLUTIONS LTD, Hod Hasharon (IL)

(72) Inventors: Ehud Kantor, Hod Hasharon (IL); Mark Shahar, Holon (IL); Nir Barkai, Kfar Saba (IL)

(73) Assignee: INOVYTEC MEDICAL SOLUTIONS LTD., Hod Hasharon (IL)

( * ) Notice: Subject to any disclaimer, the term of this patent is extended or adjusted under 35 U.S.C. 154(b) by 298 days.

(21) Appl. No.: 14/440,957

(22) PCT Filed: Nov. 10, 2013

(86) PCT No.: PCT/IL2013/050924
§ 371 (c)(1),
(2) Date: May 6, 2015

(87) PCT Pub. No.: WO2014/072981
PCT Pub. Date: May 15, 2014

(65) Prior Publication Data
US 2015/0297903 A1    Oct. 22, 2015

(30) Foreign Application Priority Data
Nov. 12, 2012    (IL) ......................................... 223004

(51) Int. Cl.
*A61N 1/39* (2006.01)
*A61M 16/06* (2006.01)
(Continued)

(52) U.S. Cl.
CPC ......... *A61N 1/3925* (2013.01); *A61M 15/009* (2013.01); *A61M 16/0003* (2014.02);
(Continued)

(58) Field of Classification Search
CPC .............. A61M 16/00; A61M 16/0463; A61M 16/049; A61M 16/06; A61M 16/0683;
(Continued)

(56) References Cited

U.S. PATENT DOCUMENTS

| | | | | |
|---|---|---|---|---|
| 4,273,114 A | * | 6/1981 | Barkalow | A61H 31/005 601/106 |
| 4,823,787 A | * | 4/1989 | Adahan | A61M 16/16 128/203.27 |

(Continued)

FOREIGN PATENT DOCUMENTS

| | | |
|---|---|---|
| CN | 2915144 Y | 6/2007 |
| CN | 201006137 Y | 1/2008 |

(Continued)

OTHER PUBLICATIONS http://www.ginasthma.org/uploads/users/files/GINA_Report2011_May4.pdf.

(Continued)

*Primary Examiner* — Valerie L Woodward
(74) *Attorney, Agent, or Firm* — McCarthy & Gruber, P.C.; Roach Brown; Kevin D. McCarthy

(57) ABSTRACT

A system that includes both an Airway and Ventilation device (AV) and an Automated External Defibrillator (AED) device is described. The system allows minimally trained persons to operate it in emergency situations involving respiratory failure and/or cardiac arrhythmias. An integral part of the AV of the system is a face mask manufactured in two parts: a face attachment unit configured to attach to the patient's face and a mask body that is releasably connected to the face attachment unit by a quick release mechanism allowing quick removal of the mask body from the face attachment unit, leaving only the face attachment unit attached to the patients' face, in order to address urgencies (Continued)

such as vomiting. After vomiting ceases and is cleared, then the mask body may be reattached to continue ventilation.

12 Claims, 5 Drawing Sheets

(51) Int. Cl.
*A61M 16/04* (2006.01)
*A61N 1/04* (2006.01)
*A61M 15/00* (2006.01)
*A61M 16/08* (2006.01)
*A61M 16/00* (2006.01)
*G06F 19/00* (2018.01)

(52) U.S. Cl.
CPC ...... *A61M 16/0057* (2013.01); *A61M 16/024* (2017.08); *A61M 16/04* (2013.01); *A61M 16/0463* (2013.01); *A61M 16/06* (2013.01); *A61M 16/0683* (2013.01); *A61M 16/08* (2013.01); *A61N 1/046* (2013.01); *A61N 1/39* (2013.01); *A61N 1/3993* (2013.01); *A61M 15/00* (2013.01); *A61M 16/049* (2014.02); *A61M 16/0816* (2013.01); *A61M 16/0833* (2014.02); *A61M 2016/0015* (2013.01); *A61M 2016/0027* (2013.01); *A61M 2016/0033* (2013.01); *A61M 2205/05* (2013.01); *A61M 2205/054* (2013.01); *A61M 2205/35* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/581* (2013.01); *A61M 2205/583* (2013.01); *A61M 2209/06* (2013.01); *A61M 2230/04* (2013.01); *A61M 2230/205* (2013.01); *A61M 2230/30* (2013.01); *A61M 2230/40* (2013.01); *A61M 2230/432* (2013.01); *A61M 2230/50* (2013.01); *G06F 19/3481* (2013.01)

(58) Field of Classification Search
CPC ..... A61M 16/08; A61M 16/0816; A61N 1/39; A61N 1/3993; A61N 1/3968; A61N 1/049; A61H 31/004–31/006
See application file for complete search history.

(56) References Cited

U.S. PATENT DOCUMENTS

| | | | |
|---|---|---|---|
| 5,231,983 A | 8/1993 | Matson et al. | |
| 6,568,388 B2 * | 5/2003 | Christopher | A61M 16/0488 128/200.26 |
| 6,827,695 B2 | 12/2004 | Palazzolo | |
| 7,152,602 B2 * | 12/2006 | Bateman | A61M 16/06 128/206.24 |
| 7,226,427 B2 * | 6/2007 | Steen | A61H 31/008 128/204.18 |
| 9,421,389 B2 | 8/2016 | Freeman | |
| 2003/0047189 A1 * | 3/2003 | Kumar | A61M 16/06 128/206.29 |
| 2004/0162510 A1 * | 8/2004 | Jayne | A61N 1/39 601/41 |
| 2004/0244799 A1 * | 12/2004 | Landis | A61M 16/0683 128/206.21 |
| 2005/0085799 A1 * | 4/2005 | Luria | A61B 5/6803 606/1 |
| 2009/0084385 A1 * | 4/2009 | Lang | A61M 16/0463 128/206.21 |
| 2010/0031963 A1 | 2/2010 | Lee | |
| 2010/0275919 A1 | 11/2010 | Sung | |
| 2012/0116272 A1 * | 5/2012 | Hampton | A61H 31/005 601/21 |

FOREIGN PATENT DOCUMENTS

| | | |
|---|---|---|
| JP | 0454971 A | 2/1992 |
| JP | 0838607 A | 2/1996 |
| JP | 2004509654 A | 4/2004 |
| JP | 2006528903 A | 12/2006 |
| JP | 2012511371 A | 5/2012 |
| WO | 93/17744 A1 | 9/1993 |
| WO | 2012065167 A1 | 5/2012 |
| WO | 2012109704 A1 | 8/2012 |

OTHER PUBLICATIONS

Lazarus SC (Aug. 2010). "Clinical practice. Emergency treatment of asthma". N. Engl. J. Med. 363(8): 755-64.

Hoek et al.; 2010 American Heart Association Guidelines for Cardiopulmonary Resuscitation and Ermergency Cardiovascular Care Science, Circulation, 2010, 122: 5829-5861.

Wik et al. 1994—"Quality of bystander cardiopulmonary resuscitation influences outcome after prehospital cardiac arrest" Resuscitation 28: 195-203.

http://www.cardiaid.com/en/Products---CPR%7CCheck/388, 2015.

Berrin G.Naydin, Pharmacotherapy in Cardiopulmonary Resuscitation (CPR), Perspectives in Medical Sciences Turk J Med Sci 35 (2005) 357-364.

International Search Report from counterpart foreign application, 4 pages, dated Feb. 20, 2014.

Written Opinion of the International Search Authority from counterpart foreign application, 6 pages, dated Feb. 20, 2014.

Japanese patent office's office action from counterpart foreign application—Japanese Patent Application No. 2015-541301; dated Jun. 30, 2017; Japanese version (5 pages) and English translation (4 pages).

Japanese patent office's office action from counterpart foreign application—Japanese Patent Application No. 2015-541301; dated Feb. 27, 2018; Japanese version (5 pages) and English translation (4 pages)—the English equivalent for JP2009526594 is U.S. Pat. No. 9,421,389.

Office action from Japanese patent office in a counterpart foreign application—JP application No. 2015-541301—dated Oct. 18, 2018, 7 pages and computer generated translations thereof (14 pages).

* cited by examiner

SYSTEM AND METHOD FOR PROVIDING NONINVASIVE VENTILATION

FIELD OF THE INVENTION

The invention is from the field of medical devices. Specifically it is from the field of medical equipment adapted to allow minimally trained operators to treat acute respiratory failure and perform CPR.

BACKGROUND OF THE INVENTION

Publications and other reference materials referred to herein, including reference cited therein, are incorporated herein by reference in their entirety and are numerically referenced in the following text and respectively grouped in the appended Bibliography which immediately precedes the claims.

Acute respiratory failure is an emergency medical condition in which there is extremely low oxygen level or extremely high carbon dioxide level in an individual's blood. In acute respiratory failure the lungs can become unable to replenish oxygen supplies because of an airway obstruction or the presence of excessive fluids. Acute respiratory failure is usually fatal if an individual does not receive immediate medical services. Doctors or emergency medical technicians will try to open a sufficient airway, supply oxygen, and determine any underlying causes in order to provide additional treatment. The onset of an acute or chronic respiratory failure may occur due to an asthma attack, smoke inhalation, choking, or drowning, or many other pulmonary diseases that obstruct the intake of air.

Respiratory failure is a common name given to a wide variety of medical situations. For example, Chronic Obstructive Pulmonary Disease (COPD) is now the third leading cause of death globally. One out of every four men and one of every six women who live to be 95 years old will develop COPD. COPD is an umbrella term used to describe lung disease associated with airflow obstruction. Most generally, emphysema, and chronic bronchitis, either alone or combined, fall into this category. In the US, there are over 1.5 million emergency department visits by adults, over 725,000 hospitalizations due to COPD and over 140,000 COPD-related deaths (2008). As of 2009, 300 million people worldwide were affected by asthma leading to approximately 250,000 deaths per year [1]. It is estimated that asthma has 7-10% prevalence worldwide [2]. Asthma is responsible for more than 2 million visits to the emergency department (ED) in the United States each year, with 1 in 4 patients requiring admission to a hospital. Annually there are 5,000 to 6,000 asthma-related deaths in the United States, many occurring in the pre-hospital setting. Severe asthma accounts for approximately 2% to 20% of admissions to intensive care units, with up to one third of these patients requiring intubation and mechanical ventilation [3].

Drowning is responsible for more than 500,000 deaths each year worldwide. Drowning is a leading preventable cause of unintentional morbidity and mortality. According to the 2010 American Heart Association Guidelines for Cardiopulmonary Resuscitation and Emergency Cardiovascular Care Science, The most important and detrimental consequence of submersion is hypoxia; therefore, oxygenation, ventilation, and perfusion should be restored as rapidly as possible Other pathologies which may result in respiratory failure include Angioedema of the airway due to Anaphylaxis; Pharyngeal infections; upper airway foreign body; Rib fractures with Flail chest; Pulmonary COPD or Asthma exacerbations; Pulmonary embolism; Pneumothorax; Pulmonary or distant infections with developed ARDS; Pulmonary contusion or other lung injury; Pulmonary insufficiency due to Cardiac failure or acute coronary syndrome; pulmonary edema; Arrhythmia; Stroke and other CNS pathologies. Oxygen is a potent and readily available treatment for many of the above causes of dyspnea and should be administered liberally.

According to the AHA 2010 guidelines, patients with severe life-threatening asthma require urgent and aggressive treatment with simultaneous administration of oxygen, bronchodilators, and steroids. Short-acting β-agonists provide rapid, dose-dependent bronchodilation with minimal side effects. Salbutamol, or albuterol, is a common short-acting Short-acting β-agonists used for the relief of bronchospasm in conditions such as asthma and chronic obstructive pulmonary disease. It is marketed as Ventolin among other brand names.

Salbutamol sulfate is commonly the form used for inhalers, for a direct effect on bronchial smooth muscle. In this form of delivery, the maximal effect of salbutamol can take place within five to 20 minutes of dosing, though some relief is immediately seen. Salbutamol is typically used to treat bronchospasm due to allergy or asthma attack, exercise-induced bronchospasm, as well as chronic obstructive pulmonary disease, and cystic fibrosis.

Systemic corticosteroids are the only treatment for the inflammatory component of asthma proven to be effective for acute asthma exacerbations. The use of inhaled steroids may hasten the resolution of airflow obstruction. In fact, Inhaled corticosteroids (ICS), or inhaled steroids, are the most potent anti-inflammatory controller medications available for the treatment of asthma. Steroids May also be extremely effective for the treatment of respiratory failure that is induced by cerebrovascular accident (CVA) also known as stroke.

Vasopressor agents that are given during CPR aim to improve aortic diastolic pressure. Consequently, increases in coronary and cerebral perfusion pressures enhance both myocardial and cerebral blood flow and improve survival. Adrenergic agonist; adrenaline (epinephrine) is routinely used to enhance cerebral and myocardial blood flow by preventing arterial collapse and by augmenting aortic diastolic pressure through alpha 1 and 2 receptors [6]. These drugs, if directly provided to the patient's mouth in the right timing, may very well be the difference between life and death.

In general, there are two types of critical care devices currently available to the public: first aid kits, including bandages and the like, and an Automated External Defibrillator (AED) being a portable electronic device that applies electrical shock therapy for the treatment of cardiac arrhythmias. Oxygen therapy equipment for active ventilation of a patient, is in most cases only available to medical professional providers of paramedics and doctors in the EMS or hospital, and is not available to non-medical personal.

In current emergency care, tracheal intubation is still the main practice for treating acute respiratory failure by paramedics and professional medical care giver. Tracheal intubation is a highly invasive and extremely uncomfortable medical procedure that requires skills, training and experience, and it is associated with significant and often fatal complications such as loss of speech, pulmonary aspiration of stomach contents, bradycardia and tracheal injury and perforation.

Non-invasive ventilation (NIV) is defined as 'delivery of ventilatory support via the patient's upper airway using a mask or similar device' and includes both continuous positive airway pressure (CPAP) and non-invasive positive pressure ventilation (NPPV). NIV was initially used to treat chronic obstructive pulmonary disease related respiratory failure and prevent the need for mechanical ventilation and the attendant complications associated with invasive ventilation but is now emerging as a useful alternative treatment strategy to mechanical ventilation in a number of different clinical situations. Worldwide, the use of NIV has more than doubled in the past 10 yr. In the UK where the previous decade has seen a disproportionate increase in level 2 critical care beds, NIV use has risen steadily. Yet, large international geographical variations remain and NIV use remains relatively low in areas such as North America.

Due to the substantial mortality and morbidity associated with tracheal intubation, the use of Non-Invasive Ventilation (NIV) is gradually increasing; currently it is mainly used in hospital wards and in the long term home care treatment of chronic respiratory problems. NIV has its own drawbacks—if the patient is unconscious NIV may not be effective enough in supplying oxygen to the patient, and, since there must be created a perfect seal to the face for keeping the air pressure inside the mask cavity, a patient who vomits may be at risk of aspiring the fluids if they are not cleared from the mask, or if the mask is not removed quickly from his face. Non-invasive ventilation is still a challenge for medical practice.

Firemen, police officers, or lifeguards acquire substantial training in basic or advanced life support. They are trained to perform CPR and use a defibrillator, and although immensely helpful, they are unable to provide emergency oxygen due to lack of appropriate solutions. Performing tracheal intubation is carried out only by highly experienced and professional medical teams in a well-equipped environment such as the ambulance or the hospital ward, while non-invasive solutions are unfortunately not available outside of such settings, e.g. in public spaces or swimming pools.

An Automated External Defibrillator (AED), which is commonly available in public spaces, is used in cases of life threatening cardiac arrhythmias which can lead to cardiac arrest. As accepted in medical practice, shockable cardiac arrhythmias include ventricular fibrillation and pulseless ventricular tachycardia (VF/VT). In both these types of shockable cardiac arrhythmia, the heart is electrically active, but in a life-threatening, dysfunctional pattern. In ventricular tachycardia, the heart beats too fast to effectively pump blood. In ventricular fibrillation, the electrical activity of the heart is chaotic, preventing the ventricles from effectively pumping blood. The AED provides electrical shock to a patient in cardiac arrhythmias (VF/VT) in order to re-synchronize the electric activity of the heart muscles, and revive the heart.

In respiratory failure, not enough oxygen is reaching the lungs to properly oxidize the blood and clear the carbon dioxide. At first, the activity of the heart remains normal, so the heart is pumping and circulating the blood throughout the body. But as the circulating blood is not oxygenated properly in the lungs due to obstruction in respiration, the oxygen blood saturation decreases rapidly, until reaching a certain low oxygen level at which the heart starts to fibrillate. Doctors refer to such fibrillation as non-cardiac VF, because this kind of fibrillation does not originate from a cardiac problem but from a respiratory problem. Although this kind of fibrillation is also treated by electric shock, the chances of surviving such non-cardiac fibrillation is much lower than in cardiac VF, as non-cardiac VF is indicative of a poor clinical situation and its success is much dependent on the oxygen level in the blood and on medications Cardiac defibrillation therapy is quite effective if applied within a short time window of 5-8 min from the time of cardiac VF/VT incidence. Studies show a 71% survival rate in witnessed cardiac arrest in casinos or airports, where AED is readily available, and the patients were treated within three minutes. After eight minutes survival rate drop dramatically.

In contrast, non-cardiac VF defibrillation has much lower chance for success, as it is the outcome of very low oxygen blood saturation and is indicative of a poor clinical condition. In fact, without restoring ventilation and elevating blood oxygen level, there is little chance of saving the patient's life.

In order to increase blood oxygen level quickly and improve the success rate of defibrillation in a non-cardiac VF, oxygen must be applied and an effective CPR must be carried out. The more effective the CPR, the faster the blood oxygen level rise until reaching a level that enables an effective shock by the AED.

The efficiency of carrying out a cardiopulmonary resuscitation (CPR) procedure is critical to the survival chances of the patient [4]. However, it is difficult to estimate CPR efficiency, especially outside a medical center.

Hence, efforts are made to assess CPR efficiency in order to improve the rate of successful CPR procedures. The company Cardiaid for example supplies a device that monitors pulse and breathing in the patient during CPR [5]. In another approach, International Patent Application WO2012/065167 discloses sensing cyclical activities by a rescuer carrying out CPR and summarizing them, and U.S. Pat. No. 6,827,695 discloses processing acceleration signals to produce an accurate estimate of the actual depth of chest compressions. These mechanical solutions try to overcome the basic problem, that vital signs are not reliable indicators as they become very chaotic and non-informative during CPR.

To summarize, as AED's are helpful in only a fraction of emergency situations, and oxygen therapy is unavailable to the non-medical care-giver, there is a pressing need for a system that can provide an integrated solution for both cardiac and respiratory emergency situations that is non-invasive and adapted to the needs of field care, and operable by minimally trained personal.

The purpose of the present invention is to provide the basically trained, semi-professional such as a life guard or police officer, with an advanced, non-invasive medical device, that supports non-invasive ventilation in an acute respiratory failure such as drowning, provides real-time feedback on CPR efficiency, optimizes the application of electric shock, and enables saving lives in a myriad of situations that were not treatable so far in an out-of-hospital field setting.

Further purposes and advantages of this invention will appear as the description proceeds.

SUMMARY OF THE INVENTION

In a first aspect the invention is a system that is provided with means for assisting only minimally trained persons to operate it in emergency situations involving respiratory failure and/or cardiac arrhythmias, the system comprising:

A. an Airway and Ventilation device (AV) comprising:
  i) a face mask comprising:
    a) a face attachment unit adapted to be attached and secured to the face contour of a patient;
    b) a mask body adapted to be releasably connected to the face attachment unit by a quick release/attachment mechanism;
    c) a hollow tube configured to provide a mouth airway securing channel;
    d) a $CO_2$ sensor, e.g. a capnograph; and
    e) a ventilation tube;
  ii) at least one sensor adapted to monitor vital signs;
  iii) a pressurized oxygen source configured to provide a flow of oxygen via the face mask and airway to the patient and to adjust the oxygen flow on the basis of the monitored vital signs;
B. an Automated External Defibrillator (AED) device comprising one or more ECG detectors that are attached to the chest of the patient and are configured to both monitor ECG and to apply electrical shock to the patient via one or more chest pads;
C. a user interface for providing audible or visual instructions to the operator;
D. components that provide communication functionality;
E. a data management unit adapted to operate the system, to provide instructions to the operator, and to record ECG and VS data the data management unit comprising:
  i) a processor;
  ii) dedicated software; and
  iii) memory units.

In embodiments of the system of the invention the AV additionally comprises at least one auxiliary ECG detector.

In embodiments of the system of the invention the sensors adapted to monitor vital signs monitor at least one of: respiration, heart rate, temperature, blood pressure, and pulse oxymeter saturation.

In embodiments of the system of the invention the AED is configured to assume control over the AV, if the ECG detectors detect VF/VT in the patient.

Embodiments of the system of the invention are adapted to activate the AV and to deactivate the AED when at least one ECG detector does not detect VF/VT in the patient.

Embodiments of the system of the invention can further comprise a compact housing adapted to package the AV and AED as well as other components. The housing can be further adapted to function as at least one of; a carrying case for transporting the components of the system; and an airway management system providing neck support for tilting the head and opening the airways, so as to ensure appropriate ventilatory respirations.

In embodiments of the system of the invention the data management unit can be located in the AV, the AED, or the housing. The data management unit can be remotely located at an emergency or medical center.

Embodiments of the system of the invention may additionally comprise at least one of: video cameras, suction units, and a location tracking unit.

In embodiments of the system of the invention the proximal end of the hollow tube of the face mask is adapted to be connected to at least one of; a catheter connected a suction unit; and an inhaler for administering a drug in a spray or aerosol form directly to the patient's mouth, the inhaler designed to have a closed body and to hermetically seal with the proximal end of the hollow tube in order to maintain the level of vacuum required for proper operation of the mask. These embodiments of the system of the invention can comprise at least one designated inhaler containing drugs to be administered to a patient, wherein the at least one designated inhaler is stored in a locked compartment which can only be opened remotely by the staff in the emergency/medical center.

In another aspect the invention is a face mask comprised of two parts:
A. a face attachment unit adapted to be attached and secured to the face contour of a patient; and
B. a mask body adapted to be releasably connected to the face attachment unit by a quick release/attachment mechanism.

The face mask of the invention can further comprise a hollow tube configured to provide a mouth airway securing channel.

Embodiments of the face mask of the invention can further comprise at least one of: a $CO_2$ sensor (e.g. a capnograph), a ventilation tube (e.g. a Y-shaped ventilation tube), a respiration sensor, and at least one connection to a suction unit.

In embodiments of the face mask of the invention comprising a hollow tube, the proximal end of the hollow tube can be adapted to be connected to at least one of: a catheter connected to a suction unit and an inhaler for administering a drug in a spray or aerosol form directly to the patient's mouth, the inhaler designed to have a closed body and to hermetically seal with the proximal end of the hollow tube in order to maintain the level of vacuum required for proper operation of the mask.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

The present invention is a system that comprises both an Airway and Ventilation device (AV) and an Automated External Defibrillator (AED) device. The system is provided with means for assisting only minimally trained persons to operate it in emergency situations involving respiratory failure and/or cardiac arrhythmias. Because of its compact nature the system of the invention can be used in hospital or ambulance settings; can be carried as part of the equipment on fire and rescue vehicles, used in field settings, e.g. by army units; or located in public venues such as sports stadiums, airports, and swimming pools.

One aspect of the present invention provides a system for enhancing cardiopulmonary resuscitation (CPR), comprising: at least one $CO_2$ sensor (capnograph) arranged to measure the $ETCO_2$ in exhalations of a patient, a processor arranged to receive the measurements from the at least one $CO_2$ sensor, and supply feedback to the caregiver whenever the measured ETCO2 is lower than a predetermined value, e.g. 10 mmHG via a user interface module. The system may also determine the ventilation state of a patient according to the number of effective chest compressions provided, the ETCO2 measured in each press, and the rhythm that the chest compressions were applied. According to the evaluation of the state of ventilation, the system may decide to apply the electric shock before the 2 minutes period recommended by the AHA. This is very important as 2 minutes is a very long time for applying strong and fast chest compressions, and many caregivers tend to tire and the chest compressions become weaker and ineffective. It is therefore highly advantageous for the system to evaluate adequate ventilation of the patient as soon as possible and apply electric shock even before 2 minutes have passed. Chest compression, even if highly effective, only produce ~20% of a normal cardiac output, therefore to restore normal cardiac output and prevent brain damage it is important to provide the shock as early as possible, but only when the patient is sufficiently ventilated in order for the shock to be effective.

Figure 1:
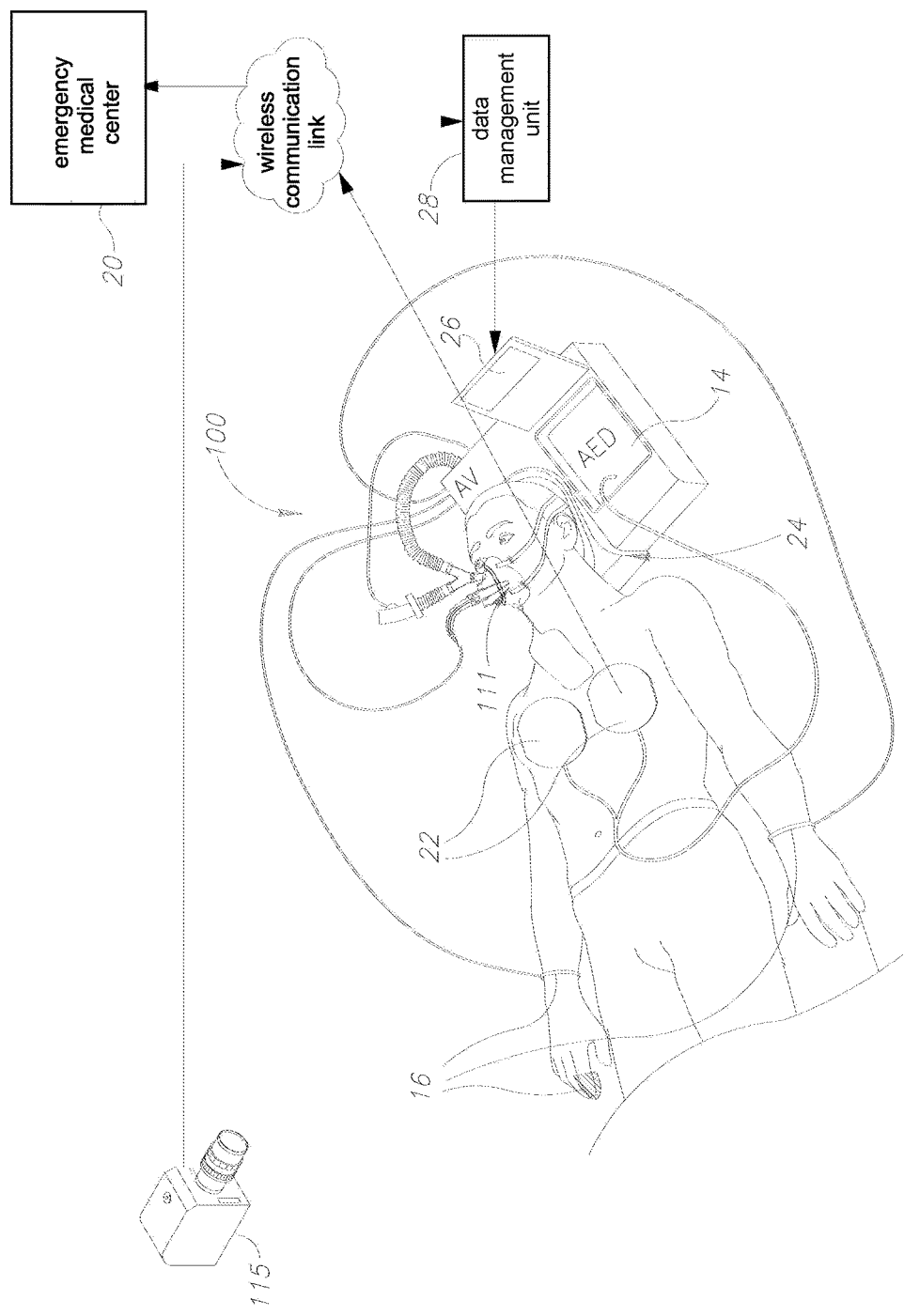
FIG. 1 schematically shows an embodiment of a system of the invention.

FIG. 1 schematically shows an embodiment of a system of the invention. Defibrillation and ventilation system 100 provides decision-assisted critical care to a patient 10 based on monitoring of vital signs (VS) and electrocardiogram (ECG) data. System 100 comprises an Airway and Ventilation device (AV) 182 and an Automated External Defibrillator (AED) device 14.

The AV 182 comprises at least one vital sign detector 16. The vital signs monitored may include respiration rate, heart rate, blood pressure, and pulse oxymetry of the patient. The vital signs detector 16 may be any device known in the art for monitoring and tracking vital signs, e.g. respiration, heart rate, temperature, blood pressure, pulse oxymeter saturation.

The ventilation device AV 182 may comprise a pressurized oxygen source and is configured to provide a flow of oxygen via a mask 111 and airway to patient 10 and to adjust the oxygen flow on the basis of the detected vital signs using a local dedicated processor and software and/or based on remote analysis or according to guidance from a remotely located emergency or medical center 20, communicated via a wireless communication link. A respiration sensor may be positioned in a reservoir of face mask 111. Data from the respiration sensor may be used to determine a respiration parameter such as an inspiration/expiration ratio, a respiratory pressure rate, and respiratory volume, and may be used as one of the acquired vital sighs (VS). Other vital signs, as well as auxiliary ECG detectors, may be acquired by detectors configured as wrist straps, or bracelets 16.

AED 14 is connected to one or more ECG detectors and patches 22 for applying shock according to the ECG readings using a local dedicated processor and software and/or based on remote analysis or according to guidance from a remotely located emergency or medical center 20, communicated via a wireless communication link. ECG detectors are attached to the chest of the patient 10 and are configured to both monitor ECG and apply electrical shock to the patient via the chest pads. AED 14 is configured to assume control over the AV 182, if the ECG detectors detect VF/VT in the patient 10. In embodiments of system 100, the AV may be activated and the AED deactivated when at least one ECG detector does not detect VF/VT in the patient 10.

System 100 may include a compact housing 24 to package the AV 182 and AED 14 as well as other components. Housing 24 can conveniently function as a carrying case for transporting the components of the system In some embodiments, housing 24 is anatomically designed to function as an airway management system providing neck support for tilting the head and opening the airways, so as to ensure appropriate ventilatory respirations.

System 100 may also include a user interface 26 for providing audible or visual instructions to the operator as well as provides sensors for measuring vital signs and communication functionality for alerting medical responders.

System 100 may further comprise a data management unit 28 comprising a processor, dedicated software, memory units and other components arranged to operate the system, provide instructions to the operator, and record ECG and VS data from AV 182, AED 14 or both. Data management unit 28 may be either local in AV 182, AED 14, or housing 24 or remote at emergency or medical center 20. A location tracking unit for determining and transmitting a geographic location of the AV 182 and AED 14 may be provided. A video camera 115 may be provided to record and transmit images of the patient 10 and system operators to the remote emergency/medical center 20 allowing trained and experienced personnel to observe what is taking place on site and to send instructions to the operators, for example by cellular phone or via user interface 26.

The processor and software of system 100 applies a method of determining the master control of the treatments, and in particular of the oxygen flow to the patient. The method basically makes AED 14 a master control over AV 12 when VF/VT is detected. If either the ECG detectors of AED 14, auxiliary ECG detectors of AV 182 or both detect VF/VT in the patient, AED 14 assumes control of AV 182 in a master-slave configuration, and applies the external defibrillation to the patient. System 100 may, in some embodiments, further be configured to release control of AV 182 by AED 14 once such control has been transferred. More specifically, in some embodiments, in a case that the auxiliary ECG detects VF/VT, but the main ECG does not, then control is returned to the AV 182. Additionally, if and only if the main ECG detects VF/VT and applies shock, then the control does not return to AV. In a case that neither of the ECG detectors of AED 14 and AV 182 respectively detect VF/VT in the patient, then the AV 182 assumes control to further detect the patient's condition through the vital signs, induces the flow of oxygen, and guides the caregiver to further assist the patient based on the detected vital signs. In embodiments, the AV 182 may be activated and the AED 14 deactivated when at least one main ECG detector does not detect VF/VT in the patient.

Figure 2A:
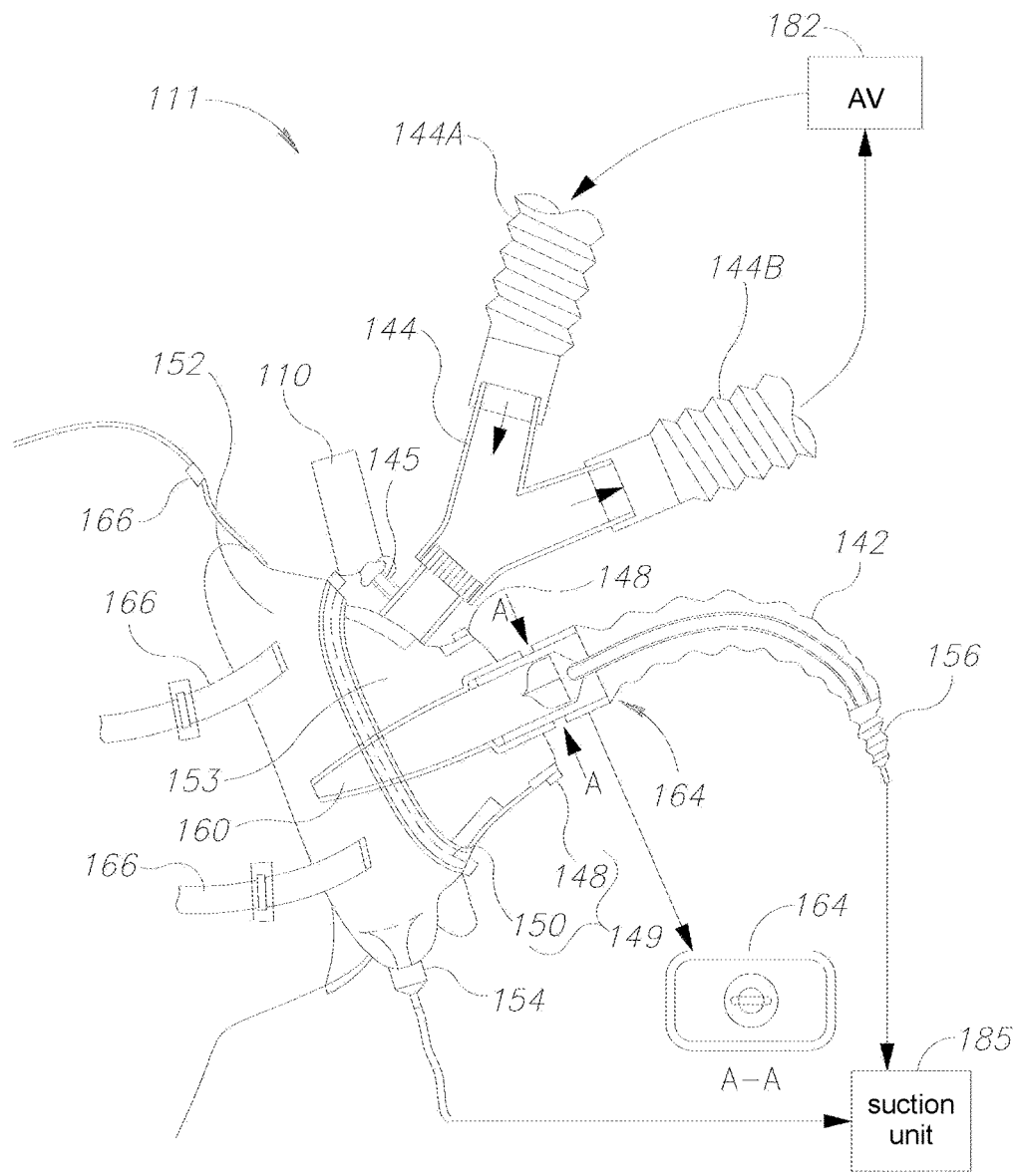
FIG. 2A schematically shows a face mask that is an integral part of the system of the invention.
Figure 2B:
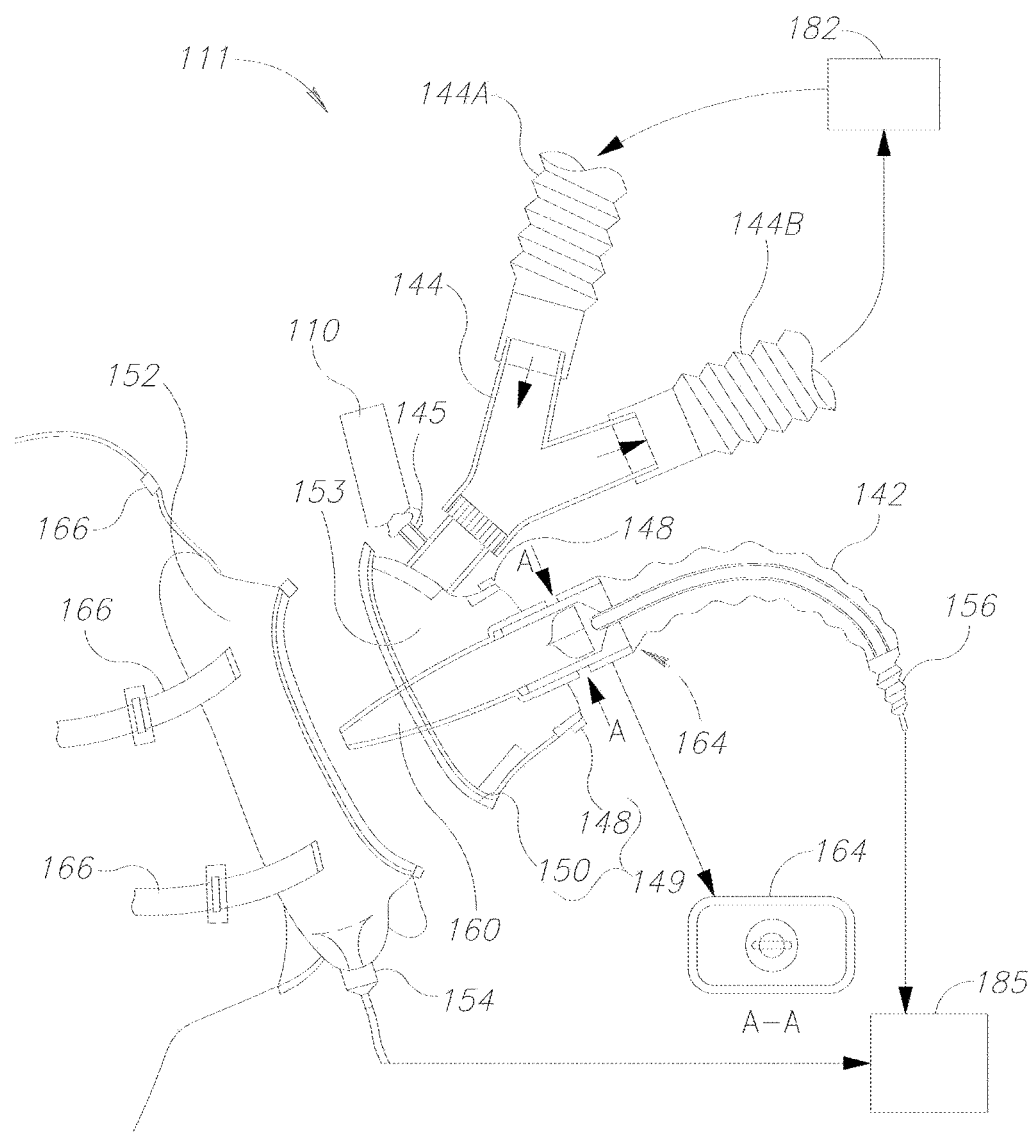
FIG. 2B schematically shows the two parts of the facemask of the invention separated from each other.

FIG. 2A schematically shows face mask 111 that is an integral part of AV 182 of system 100 for providing non-invasive ventilation in ambulance, hospital wards, long-term home care and also in a field setting, according to some embodiments of the invention. Non-invasive mask interface 111 is comprised of two parts: a face attachment unit 152 and a mask body 153. FIG. 2B schematically shows the two parts of the face-mask of the invention separated from each other.

Face attachment unit 152 attaches to the patient's face and is secured to the face by connectors 166 that ensure a tight fitting of attachment unit 152 to the face contour. Attachment unit 152 may be made e.g. of silicone. It may comprise an inflatable liner to ensure sealing to the patient's face. Face attachment unit 152 may include a secondary suction port 154 that can be connected to suction unit 185 to clear fluids that pool at the bottom of the mask cavity.

The mask body 153 is releasably connected to the face attachment unit 152 by a quick release mechanism 149, e.g. comprised of connectors 150 and release buttons 148, for the quick removal of the mask body from the face attachment unit, leaving only the face attachment unit attached to the patients' face, in order to address urgencies such as vomiting. After vomiting ceases and is cleared, then the mask body may be reattached via connector 150 to continue ventilation.

Mask body 153 comprises a capnograph 110 arranged to measure the CO2 level in the exhaled air, a hollow tube 160 that provides a mouth airway securing channel 164 arranged to maintain an open airway for the patient to effectively inhale the applied oxygen.

Capnograph 110 is arranged to measure the ETCO2 in the exhaled air in order to provide the care giver with a specific feedback on the efficiency of the CPR and chest compressions. ETCO2 data is also used in order to optimize the timing for applying electric shock by the defibrillator to improve the success rate of defibrillation in non-cardiac fibrillation and shorten the time of chest compression until an effective shock can be applied, in order to prevent brain damage and caregiver fatigue.

Figure 2C:
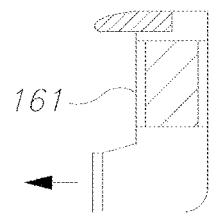
FIG. 2C schematically shows a designated inhaler that can be used with the face mask of the invention.
Figure 2D:
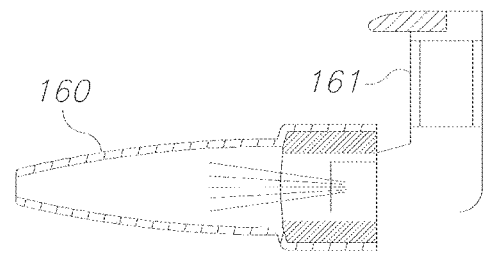
FIG. 2D shows the inhaler of FIG. 2C connected to the proximal end of a mouth airway securing channel of the face mask of FIG. 2A.

Being hollow, tube 160 may have additional functions, such as providing a passageway for the suction of secretions or for administering a spray or aerosol drug directly to the patient's mouth for maximum effect. For suction, catheter 142 connects to the proximal end of mouth airway securing channel 164 and to a suction unit 185 via connector 156. Suction unit 185 may be an integral part of AV 182 or a separate unit, for example, located inside housing 24. For administering a drug, a designated inhaler 161 (shown in FIG. 2C) connects to the proximal end of mouth airway securing channel 164 as shown in FIG. 2D. The inhaler 161 is designed to have a closed body and to hermetically seal with the proximal end of mouth airway securing channel 164, in order to prevent pressure from escaping the mask through the inhaler. The inhaler 161 is designed to release a drug in a spray or aerosol form directly to the patient's mouth, while maintaining the level of vacuum required for proper operation of mask 111. The inhaler 161 may be a manual inhaler, an automatic inhaler or a medicine administrating inhaler, and further comprise a sealing valve. For example, the proximal end of mouth airway securing channel 164 may have a rectangular outer cross section (shown in the inset labeled A-A in FIG. 2A) that provides a sealed connection to either an inhaler 161 or catheter 142. In this way the mask cavity is kept sealed to maintain effective ventilation and CO2 measurement, as well as administering drugs, and removing liquids from the interior of mask 111.

In some aspects of the present invention the system may identify the need for a medication and suggest to the caregiver to administer the appropriate drug. If a physician's approval is required for the administering of a certain drug, the system may ask the remote medical center to approve the administration of a drug to the patient. In some embodiments of the system 100 of the invention, one or more designated inhalers containing the appropriate drugs are stored in a locked compartment in system which can only be opened remotely by the staff in the emergency/medical center.

Mask body 153 also comprises the ventilation tubes, a Y-shaped tube 144 connected to portable ventilator 182 that delivers air or oxygen via one arm 144A and removes the exhaled air via a second arm 144B. Additionally, face mask 111 or Y-formed tube 144 may include a connector (not shown) for a lung pressure meter, used to ensure that the patient's lungs are not at risk of collapsing. System 100 may further comprise a lung pressure meter arranged to monitor lung pressure.

In embodiments, the ventilation procedure may be remotely supervised via camera 115, and the caregiver may be guided by the supervising emergency/medical center 20. Camera 115 is arranged to visually monitor the entire care session, including the application of chest compression and the administration of medication. The audio and video data are transferred to a data management unit 28 and transferred to an emergency/medical center 20 for on-line medical support.

Figure 3:
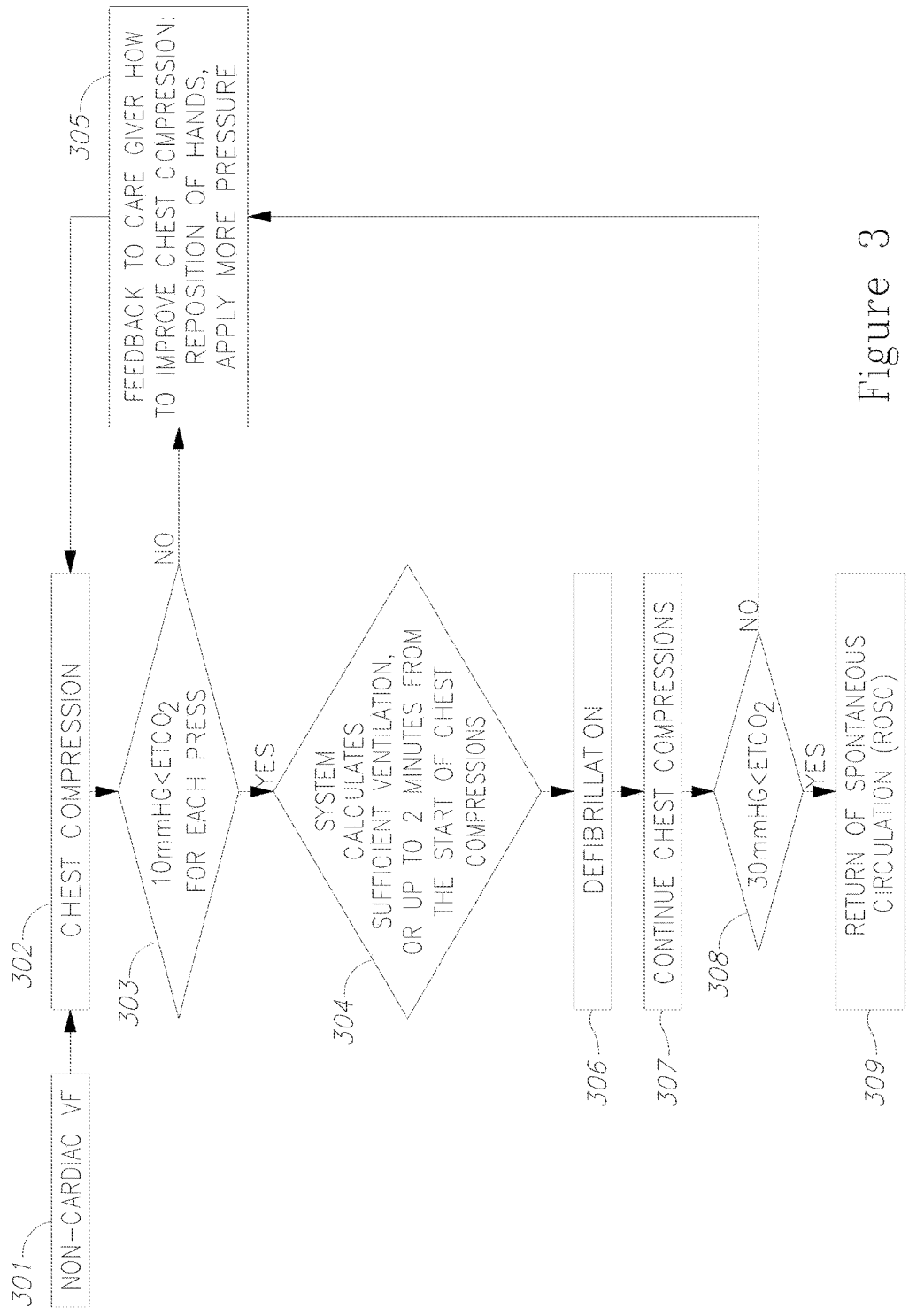
FIG. 3 is a flow chart showing the principle steps a method for using the system of the invention to treat non-cardiac VF by performing CPR.

FIG. 3 is a flow chart showing the principle steps a method for using the system of the invention to treat non-cardiac VF by performing CPR according to the measured levels of ETCO2 (end tidal CO2). Once Non-cardiac VF is detected by the ECG 301, the caregiver is instructed to start chest compression on the patient 302. The capnograph senses the partial pressure of carbon dioxide ($CO_2$) at the end of an exhaled breath, expressed as mmHg. If the measured $ETCO_2$ is greater than 10 mmHG in each breath, then this is indicative of effective chest compressions and the method proceeds to step 304. If not, then feedback is provided to the caregiver on how to improve the chest compressions, such as how to relocate the hands and apply more pressure 305. According to the AHA guidelines, once 2 minutes have passed from the commencement of chest compressions, an electric shock must be applied to the patient. These guidelines were made for a non-monitored environment; but, as the system of the invention monitors the ETCO2 in each press, a much better estimation of the state of ventilation of the patient can be made. Therefore the system is able to determine when sufficient ventilation has taken place for applying an electric shock to the patient well before two minutes have passed 304. Shortening the compression time is important for preventing brain damage for the patient. Since applying intensive and fast chest compression for two full minutes can be very challenging to most people, it is also important to shorten compression time also to prevent caregiver fatigue. Once two minutes have past, or the system calculates and determines that sufficient ventilation has occurred, the caregiver is instructed to stay clear from the patient and electric shock is provided to the patient 306. According to the AHA guidelines the caregiver is supposed to continue chest compressions immediately after the shock is applied 307. When the system measures ETCO2 above 30 mm Hg, it instructs the caregiver to stop compressions 308 due to Return of Spontaneous Circulation (ROSC) 309. If the system measures ETCO2 below 30 mm Hg, then the method returns to step 305.

Figure 4:
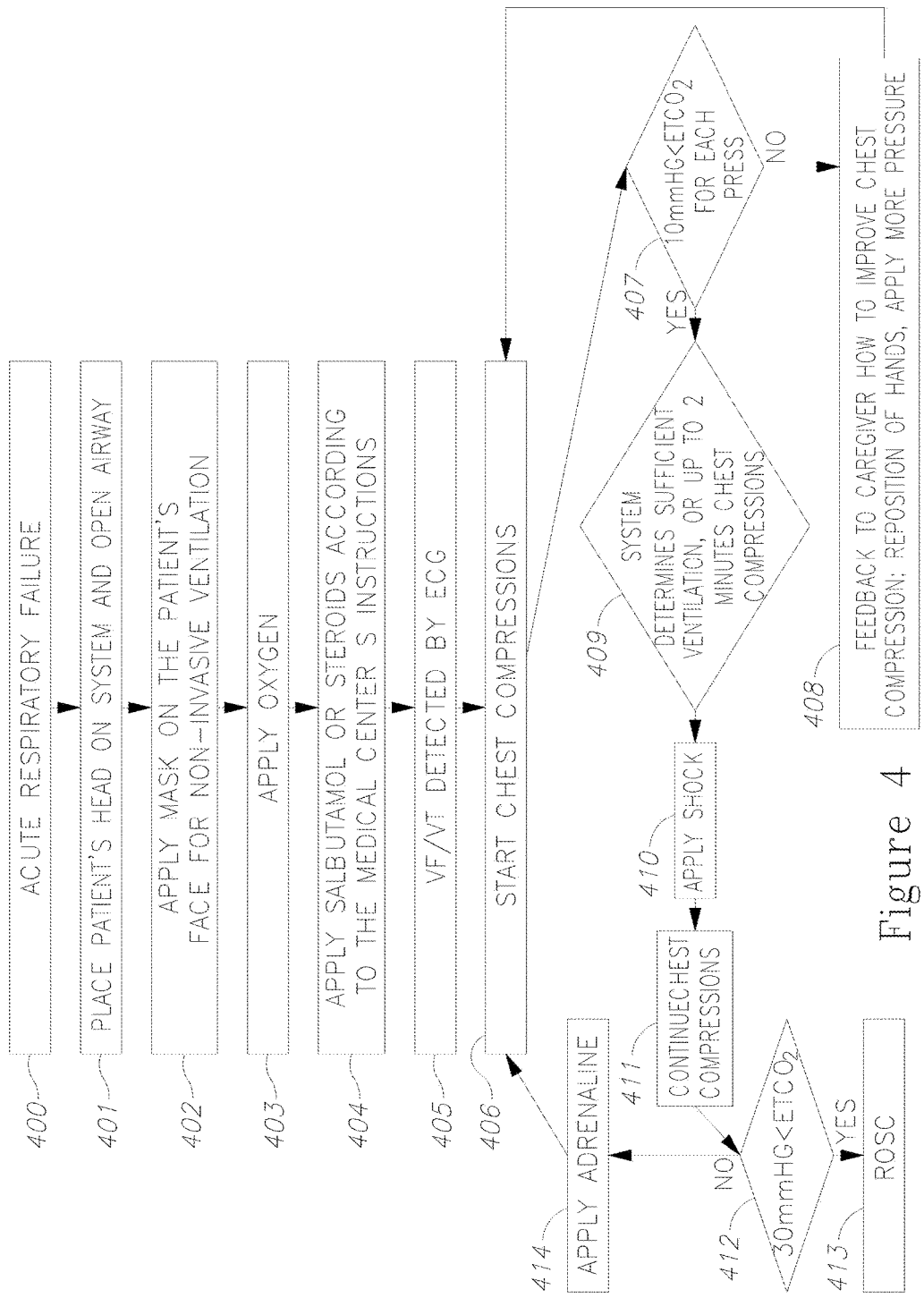
FIG. 4 is a flow chart showing the principle steps of a method for using the system of the invention to treat acute respiratory failure.

FIG. 4 is a flow chart showing the principle steps of a method for using the system of the invention to treat acute respiratory failure according to embodiments of the present invention.

The very first actions required when acute respiratory failure is detected 400 are to open an airway and supply oxygen. The patient is placed on an airway management unit for head tilt and to open an airway 401. Then a non-invasive ventilation mask interface is applied to the patient's face 402. The face mask 111 can either be applied as a single unit or in two stages—applying the face attachment unit 152 first and, after it is well secured to the face, the mask body 153 may be attached to face attachment unit 152. Then the application of oxygen to the patient begins 403. According to instructions received from the emergency/medical center 20, a medication, possible from the group comprising a bronchodilators (Salbutamol) or steroids, may now be applied to the patient's mouth 404. In a severe asthma or allergy attack, these actions alone may save the patient's life. If the oxygen level of the patient continues to drop, and VF/VT is detected by the ECG 405, then the caregiver is instructed by the data management unit 28 or the emergency/medical center 20 to begin chest compressions 406. If the measured ETCO$_2$ is lower than 10 mm Hg 407, then feedback is provided to the caregiver via the user interface prompts 26 on how to improve the chest compressions, such as how to relocate the hands and apply more pressure 408. If the measured ETCO2 is greater than 10 mm Hg 407, then once the system determines sufficient ventilation, or if two minutes have passed 409, the caregiver is instructed to stay clear from the patient and electric shock is provided to the patient 410. The caregiver is instructed to continue chest compressions immediately after the shock is applied 411. When the system measures ETCO2 above 35 mmHg 412, it instructs the caregiver to stop compressions due to Return of Spontaneous Circulation (ROSC) and successful CPR 413. If the system measures ETCO2 below 35 mmHg 411, instructions are sent from the emergency/medical center 20 to the caregiver to apply Vasopressor (i.e. adrenaline) to the patient 414 and to continue with chest compressions 406.

Although embodiments of the invention have been described by way of illustration, it will be understood that the invention may be carried out with many variations, modifications, and adaptations, without exceeding the scope of the claims.

BIBLIOGRAPHY 1. http://www.ginasthma.org/uploads/users/files/GINA_Report2011_May 4.pdf
2. Lazarus S C (August 2010). "Clinical practice. Emergency treatment of asthma". N. Engl. J. Med. 363(8): 755-64.
3. http://circ.ahajournals.org/content/122/18_suppl_3/S829.full
4. Wik et al. 1994—"Quality of bystander cardiopulmonary resuscitation influences outcome after prehospital cardiac arrest." Resuscitation 28: 195-203.
5. http://www.cardiaid.com/en/Products—CPR %7CCheck/388.
6. Berrin G. NAYDIN, Pharmacotherapy In Cardiopulmonary Resuscitation (CPR), PERSPECTIVES IN MEDICAL SCIENCES Turk J Med Sci 35 (2005) 357-364.

The invention claimed is:

1. A system configured to assist minimally trained persons to operate it to provide treatment in emergency situations involving respiratory failure and/or cardiac arrhythmias, said system comprising:
    A) an Airway and Ventilation device (AV) comprising:
        i) a face mask;
        ii) at least one sensor adapted to monitor vital signs (VS);
        iii) a pressurized oxygen source configured to provide a flow of oxygen via said face mask and an airway to a patient and to adjust the oxygen flow on the basis of said monitored vital signs;
    B) an Automated External Defibrillator (AED) device comprising one or more electrocardiogram (ECG) detectors that are adapted to be attached to the chest of said patient and are configured to both monitor ECG and to apply electrical shock to said patient via one or more chest pads;
    C) a user interface for providing audible or visual instructions to an operator;
    D) components that provide communication functionality;
    E) a data management unit adapted to operate said system, to provide instructions to the operator, and to record ECG and VS data said data management unit comprising:
        i) a processor;
        ii) dedicated software; and
        iii) memory units;
    characterized in that the face mask comprises:
        a) a face attachment unit configured to be attached and secured to the face of a patient by means of connectors that ensure a tight fitting of the face attachment unit to the face contours;
        b) a mask body configured to be releasably connected to said face attachment unit by a quick release/attachment mechanism;
        wherein said face mask body comprises:
            i) a hollow tube that passes from the interior side to the exterior side of said face mask body and is configured to provide a mouth airway securing channel;
            ii) a CO$_2$ sensor configured to measure end tidal CO$_2$ (ETCO$_2$) in exhalations of said patient; and
            iii) a ventilation tube connected to a portable ventilator configured to deliver air or oxygen to said patient and to remove exhaled air from said patient; and
        wherein said quick release/attachment mechanism is configured to allow quick removal of said mask body from said face attachment unit, leaving only the face attachment unit attached by the connectors to the patients' face and leaving the mouth and nose of the patient exposed to the surroundings; and
    additionally characterized in that the processor and dedicated software are configured to determine when to apply electric shock according to evaluation of the state of ventilation, wherein the state of ventilation is evaluated according to the ETCO$_2$ measured in each chest compression applied by the operator to the patient.

2. The system of claim 1, wherein the AV additionally comprises at least one auxiliary ECG detector.

3. The system of claim 1, wherein the at least one sensor is adapted to monitor vital signs monitors at least one of: respiration, heart rate, temperature, blood pressure, and pulse oxymeter saturation.

4. The system of claim 1, wherein the AED is configured to assume control over the AV, if the ECG detectors detect ventricular fibrillation and pulseless ventricular tachycardia (VF/VT) in the patient.

5. The system of claim 1, adapted to activate the AV and to deactivate the AED when at least one ECG detector does not detect ventricular fibrillation and pulseless ventricular tachycardia (VF/VT) in the patient.

6. The system of claim 1, further comprising a compact housing adapted to package the AV and AED as well as other components; said housing further adapted to function as at least one of:
    A) a carrying case for transporting the components of the system; and
    B) an airway management system providing neck support for tilting the head and opening the airways.

7. The system of claim 1, wherein the data management unit is located in the AV, the AED, or a housing.

8. The system of claim 1, wherein the data management unit is remotely located at an emergency or medical center.

9. The system of claim 1, additionally comprising at least one of: video cameras, suction units, and a location tracking unit.

10. The system of claim 1, wherein the proximal end of the hollow tube of the face mask is adapted to be connected to at least one of:
   A) a catheter connected to a suction unit; and
   B) an inhaler for administering a drug in a spray or aerosol form directly to the patient's mouth, said inhaler designed to have a closed body and to hermetically seal with said proximal end of said hollow tube in order to maintain the level of vacuum required for proper operation of said mask.

11. The system of claim 10, comprising at least one designated inhaler containing drugs to be administered to a patient, wherein said at least one designated inhaler is stored in a locked compartment which is only capable of being opened by a staff member in an emergency/medical center.

12. The system of claim 1, wherein the state of ventilation is additionally evaluated according to at least one of: the number of effective chest compressions provided and the rhythm that the chest compressions were applied.

* * * * *

UNITED STATES PATENT AND TRADEMARK OFFICE
CERTIFICATE OF CORRECTION

| | |
|---|---|
| PATENT NO. | : 10,245,437 B2 |
| APPLICATION NO. | : 14/440957 |
| DATED | : April 2, 2019 |
| INVENTOR(S) | : Kantor et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 490 days.

Signed and Sealed this
Sixth Day of December, 2022

Katherine Kelly Vidal
*Director of the United States Patent and Trademark Office*